US00PP22007P2

(12) United States Plant Patent
Herrera Valenzuela et al.

(10) Patent No.: US PP22,007 P2
(45) Date of Patent: Jul. 5, 2011

(54) ***ALSTROEMERIA* PLANT NAMED 'JALUA'**

(50) Latin Name: *Alstroemeria hybrida*
Varietal Denomination: Jalua

(75) Inventors: Camilo Herrera Valenzuela, Bogotá (CO); Henry Belalcázar Valencia, Bogotá (CO)

(73) Assignee: C. I. Valmar S.A., Bogotá (CO)

( * ) Notice: Subject to any disclaimer, the term of this patent is extended or adjusted under 35 U.S.C. 154(b) by 0 days.

(21) Appl. No.: 12/660,106

(22) Filed: Feb. 19, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner* — June Hwu
(74) *Attorney, Agent, or Firm* — C. A. Whealy

(57) ABSTRACT

A new and distinct cultivar of *Alstroemeria* plant named 'Jalua', characterized by its erect and strong flowering stems; vigorous growth habit; large light red purple and yellow-colored flowers with purple-colored flecks and streaks, flowers arranged in symmetrical umbels; and excellent postproduction longevity.

1 Drawing Sheet

Botanical designation: *Alstroemeria hybrida.*
Cultivar denomination: 'JALUA'.

BACKGROUND OF THE INVENTION

The present invention relates to a new and distinct cultivar of Alstroemeria plant, botanically known as *Alstroemeria hybrida,* commercially used as a cut flower *Alstroemeria,* and hereinafter referred to by the name 'Jalua'.

The new Alstroemeria plant is a product of a planned breeding program conducted by the Inventors in Madrid, Cundinamarca, Colombia. The objective of the breeding program was to create new *Alstroemeria* cultivars with desirable plant qualities, attractive flower color and excellent postproduction longevity.

The new *Alstroemeria* plant originated from a cross-pollination conducted by the Inventors in Madrid, Cundinamarca, Colombia in June, 2002 of a proprietary selection of *Alstroemeria hybrida* identified as code number JA 812, not patented, as the female, or seed, parent with a proprietary selection of *Alstroemeria hybrida* identified as code number JA 538, not patented, as the male, or seed, parent. The new *Alstroemeria* plant was discovered and selected by the Inventors as a single flowering plant from within the progeny of the stated cross-pollination grown in a controlled greenhouse environment in Madrid, Cundinamarca, Colombia in April, 2003.

Asexual reproduction of the new *Alstroemeria* plant by rhizome divisions in a controlled greenhouse environment in Madrid, Cundinamarca, Colombia since May, 2003, has shown that the unique features of this new *Alstroemeria* plant are stable and reproduced true to type in successive generations.

SUMMARY OF THE INVENTION

Plants of the new *Alstroemeria* have not been observed under all possible environmental and cultural conditions. The phenotype may vary somewhat with variations in environment and cultural practices such as temperature and light intensity without, however, any variance in genotype.

The following traits have been repeatedly observed and are determined to be the unique characteristics of 'Jalua'. These characteristics in combination distinguish 'Jalua' as a new and distinct cultivar of Alstroemeria plant:

1. Erect and strong flowering stems.
2. Vigorous growth habit.
3. Large light red purple and yellow-colored flowers with purple-colored flecks and streaks, flowers arranged in symmetrical umbels.
4. Excellent postproduction longevity.

Plants of the new *Alstroemeria* can be compared to plants of the parent selections. Plants of the new *Alstroemeria* differ from plants of the parent selections primarily in flower color as plants of the female parent selection have orange and yellow orange-colored flowers and plants of the male parent selection have purple-colored flowers.

Plants of the new *Alstroemeria* can be compared to plants of *Alstroemeria hybrida* 'Garima', not patented. In side-by-side comparisons plants of the new *Alstroemeria* differed primarily from plants of 'Garima' in the following characteristics:

1. Plants of the new *Alstroemeria* had larger umbels than plants of 'Garima'.
2. Plants of the new *Alstroemeria* had fewer flowers per inflorescence than plants of 'Garima'.
3. Plants of the new *Alstroemeria* had larger flowers than plants of 'Garima'.
4. Plants of the new *Alstroemeria* and 'Garima' differed in flower color as plants of 'Garima' had paler pink-colored flowers with creamy white-colored centers.
5. Plants of the new *Alstroemeria* had longer pedicels than plants of 'Garima'.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria* plant.

The photograph at the bottom of the sheet comprises a side perspective view of a typical flowering stem of 'Jalua'.

The photograph at the top of the sheet is a close-up view of a typical inflorescence of 'Jalua'.

DETAILED BOTANICAL DESCRIPTION

The aforementioned photographs and following observations and measurements describe plants of the new *Alstroemeria* grown in Madrid, Cundinamarca, Colombia in a polyethylene-covered greenhouse in ground beds. During the production of the plants, maximum day temperatures averaged 31.5° C., maximum night temperatures averaged 6° C. and light levels averaged 21.4 KWH/m$^2$. Plants used for the photographs and description were two years old. Color references are made to The Royal Horticultural Society Colour Chart, 2007 Edition, except where general terms of ordinary dictionary significance are used.

Botanical classification: *Alstroemeria hybrida* 'Jalua'.

Parentage:

*Female, or seed, parent.*—Proprietary selection of *Alstroemeria hybrida* identified as code number JA 812, not patented.

*Male, or pollen, parent.*—Proprietary selection of *Alstroemeria hybrida* identified as code number JA 538, not patented.

Propagation:

*Type.*—By rhizome divisions.

*Time to initiate roots.*—About two weeks at temperatures ranging from about 6° C. to 32° C.

*Time to produce a rooted young plant.*—About eight weeks at temperatures ranging from about 6° C. to 32° C.

*Root description.*—Fleshy, medium in thickness; close to 155A in color.

*Rooting habit.*—Freely branching; dense.

*Rhizomes.*—Shape: Rounded. Length: About 6 cm. Diameter: About 1.15 cm. Texture: Fleshy. Color: Close to 155C.

Plant description:

*Plant and growth habit.*—Upright; freely branching, bushy appearance; vigorous growth habit.

*Time from planting to harvest of cut flowers.*—About 21 weeks.

Flowering stem description:

*Aspect.*—Erect.

*Length.*—About 120 cm to 130 cm.

*Diameter.*—About 6 mm.

*Internode length.*—About 2.6 cm to 4 cm.

*Strength.*—Strong.

*Texture.*—Smooth, glabrous.

*Color.*—Close to 144A.

Foliage description:

*Arrangement.*—Alternate, simple.

*Length.*—About 12 cm.

*Width.*—About 3 cm.

*Shape.*—Oblanceolate.

*Apex.*—Acute.

*Base.*—Attenuate.

*Margin.*—Entire.

*Texture, upper and lower surfaces.*—Smooth, glabrous; longitudinally ridged.

*Venation pattern.*—Parallel.

*Color.*—Developing leaves, upper and lower surfaces: Close to 146C. Fully expanded leaves, upper surface: Close to N137B; venation, close to 146B. Fully expanded leaves, lower surface: Close to 146B; venation, close to 146C.

*Petioles.*—Length: About 4.5 cm. Diameter: About 7 mm. Texture, upper and lower surfaces: Smooth, glabrous. Color, upper and lower surfaces: Close to 146C.

Flower description:

*Flower type and arrangement.*—Single cup-shaped flowers arranged in compound umbels; flowers face upright to outwardly; perianth segments separate.

*Flowering habit.*—Freely flowering with about 15 open flowers and flower buds per inflorescence.

*Natural flowering season.*—Flowering continuous year round in a greenhouse in Colombia; plants begin flowering about 21 weeks after planting.

*Fragrance.*—None detected.

*Flower longevity as a cut flower.*—About two weeks; flowers not persistent.

*Flower buds* (*showing color*).—Length: About 4.7 cm. Diameter: About 1.5 cm. Shape: Obovate. Color: Close to 145D; towards the apex, close to 145A tinted with close to 37C to 37D.

*Umbel height.*—About 28 cm to 30 cm.

*Umbel diameter.*—About 22 cm by 25 cm.

*Flower diameter.*—About 7 cm.

*Flower length* (*height*).—About 7.5 cm.

*Flower depth.*—About 9 cm.

*Perianth.*—Arrangement: Six arranged in two whorls, each whorl with two lateral and one median segments. Inner perianth, lateral segments: Length: About 7.7 cm. Width: About 2.4 cm. Shape: Oblanceolate. Apex: Apiculate. Base: Attenuate. Margin: Entire; towards the apex, slightly sinuate. Texture, upper and lower surfaces: Smooth, glabrous; satiny. Color, when opening, upper surface: Close to 62B; mid-section, close to 13C; towards the base, close to 155D; flecks and streaks, close to 183C. Color, when opening, lower surface: Close to 62C; mid-section, close to 8B; towards the base, close to 155D. Color, fully opened, upper surface: Close to 63C with flecks, close to 63A; mid-section, close to 14B; towards the base, close to 155D; flecks and streaks, close to 185A. Color, fully opened, lower surface: Close to N66D; mid-section, close to 14C; towards the base, close to 155D. Inner perianth, median segment: Length: About 6.7 cm. Width: About 2.3 cm. Shape: Oblanceolate. Apex: Apiculate. Base: Attenuate. Margin: Entire; towards the apex, slightly sinuate. Texture, upper and lower surfaces: Smooth, glabrous; satiny. Color, when opening, upper surface: Close to 62B; mid-section, close to 62D; towards the base, close to 155D. Color, when opening, lower surface: Close to 65B to 65C; towards the base, close to 155D. Color, fully opened, upper surface: Close to 63C with flecks, close to 63A; mid-section, close to 12B; towards the base, close to 155D; few flecks and streaks, close to 185A. Color, fully opened, lower surface: Close to 63C; mid-section, close to 13D; towards the base, close to 155D. Outer perianth, lateral segments: Length: About 6.9 cm. Width: About 3.3 cm. Shape: Obovate to cordate. Apex: Emarginate to cordate. Base: Attenuate. Margin: Entire; towards the apex, slightly senate. Texture, upper and lower surfaces: Smooth, glabrous. Color, when opening, upper surface: Close to 63D; at the apex, close to 147D; towards the base, close to 155D. Color, when opening, lower surface: Close to 65C; at the apex, close to 146B; towards the base, close to 155D. Color, fully opened, upper surface: Close to 65A to 65B; towards the base, close to 155B. Color, fully opened, lower surface: Close to 63C; at the apex and venation, close to 146C. Outer perianth, median segment: Length: About 6.7 cm. Width: About 3.2 cm. Shape: Obovate to cordate. Apex: Emarginate to cordate. Base: Attenuate. Margin: Entire; towards the apex, slightly serrate. Texture, upper and lower surfaces: Smooth, glabrous. Color, when opening, upper surface: Close to 63D; at the apex, close to 147C; towards the base, close to 155D. Color, when opening, lower surface: Close to 65C; at the apex, close to 146B; towards the base, close to 155D. Color, fully opened, upper surface: Close to 63C; at the apex, close to 146C; towards the base, close to 155B; color becoming closer to 62C to 62D with development. Color, fully opened, lower surface: Close to 63C; at the apex and venation, close to 146C; color becoming closer to 62C to 62D with development.

*Pedicels.*—Length: About 8 cm. Diameter: About 2.5 mm. Strength: Strong. Angle: About 15° to 25° from the peduncle axis. Texture: Smooth, glabrous. Color: Close to 146C.

*Reproductive organs.*—Stamens: Quantity per flower: Six. Anther shape: Elongated. Anther length: About 9 mm. Anther diameter: About 2.5 mm. Anther color: Close to 160A. Pollen amount: Moderate. Pollen color: Close to 12A. Pistils: Quantity per flower: One. Pistil length: About 6.5 cm. Style length: About 5 cm. Style color: Close to 69C to 69D. Stigma shape: Three-parted. Stigma color: Close to 65C. Ovary color: Close to 146C.

*Fruit/seed.*—Fruit and seed development has not been observed.

Disease/pest resistance: Plants of the new *Alstroemeria* have not been observed to be resistant to pathogens and pests common to *Alstroemeria*.

It is claimed:

1. A new and distinct *Alstroemeria* plant named 'Jalua' as illustrated and described.

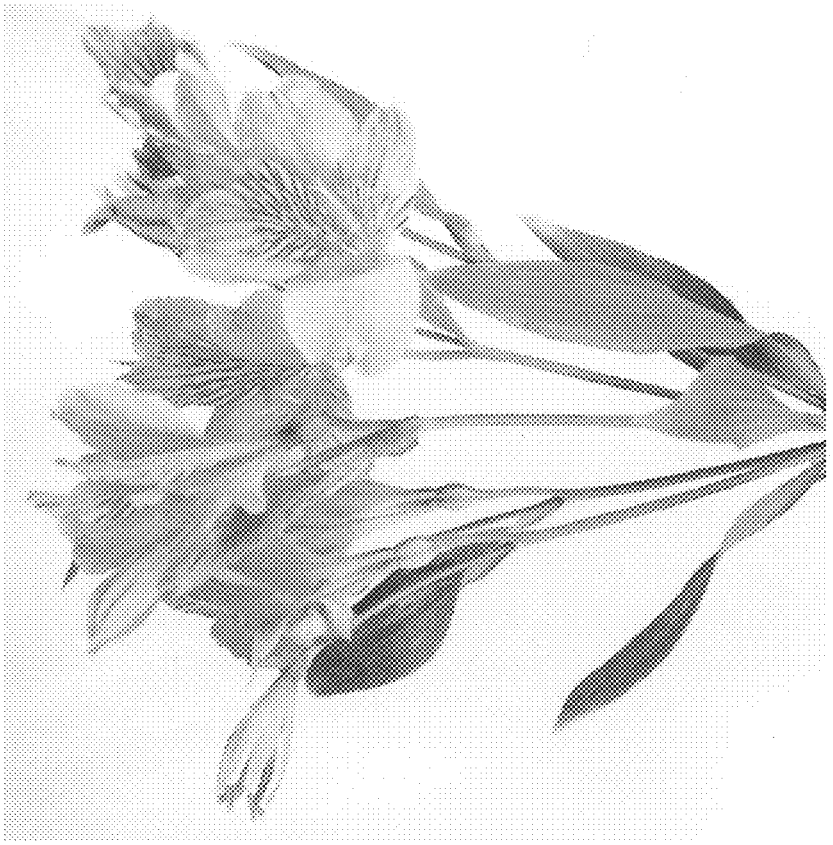
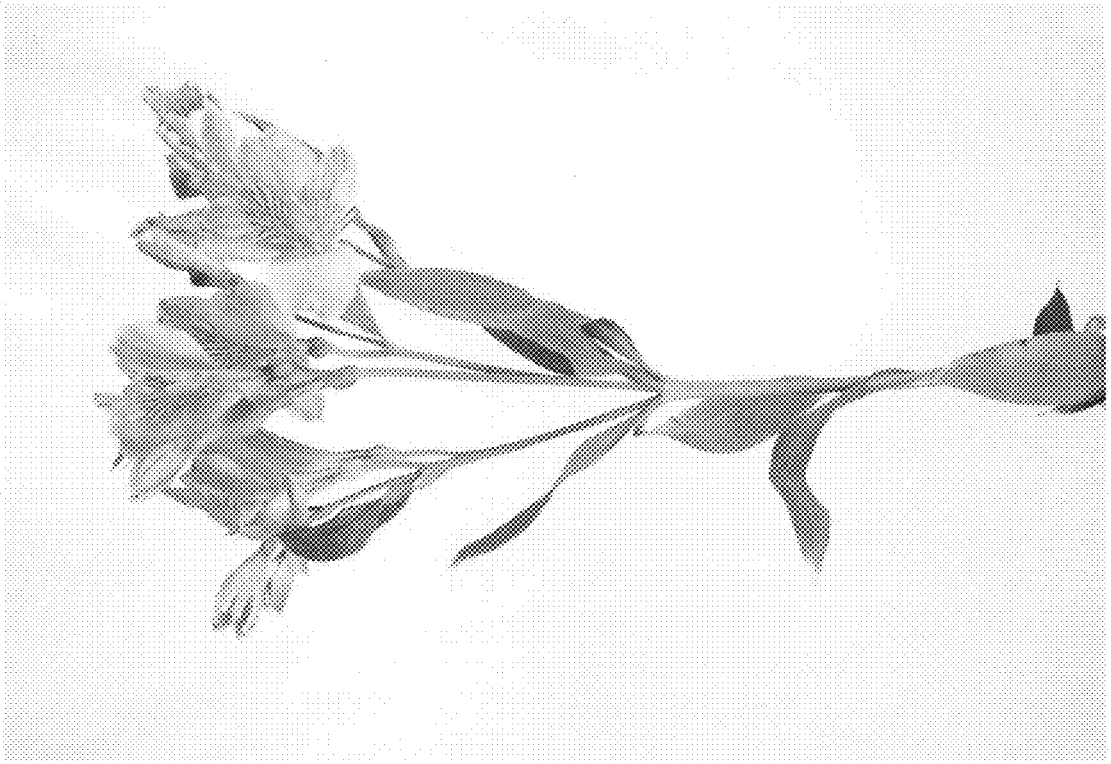

* * * * *